US006596015B1

(12) United States Patent
Pitt et al.

(10) Patent No.: US 6,596,015 B1
(45) Date of Patent: Jul. 22, 2003

(54) METHODS AND APPARATUS FOR ANNEALING SUTURES

(75) Inventors: Duane D. H. Pitt, Scottsdale, AZ (US); Christopher M. Jobe, Redlands, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 152 days.

(21) Appl. No.: 09/615,435

(22) Filed: Jul. 13, 2000

Related U.S. Application Data
(60) Provisional application No. 60/143,532, filed on Jul. 13, 1999.

(51) Int. Cl.$^7$ .............................................. A61B 17/04
(52) U.S. Cl. ...................................................... 606/232
(58) Field of Search ................................ 606/144, 151, 606/157, 219, 220, 228, 232, 222

(56) References Cited

U.S. PATENT DOCUMENTS

| | | | |
|---|---|---|---|
| 4,602,635 A | * | 7/1986 | Mulhollan et al. .......... 606/144 |
| 4,845,851 A | | 7/1989 | Warthen |
| 5,417,700 A | * | 5/1995 | Egan ........................... 606/103 |
| 5,728,109 A | * | 3/1998 | Schulze et al. .............. 289/1.2 |

OTHER PUBLICATIONS

Benson B. Roe, M.D., and Paul B. Kelly, Jr., M.D., *Heat Fusion of Synthetic Suture Knots During Prosthetic Valve Implantation*, 1 Ann Thorac Surg 775–777 (1965).

Thomas M. Masterson, M.D., et al, *Heat Welding for Surgical Sutures*, 150 Am. J. Surg. 318–320 (1985).

Jared P. Tadje, et al., *Enhancing Knot Security by Heat Treatment of Knot Ears*, 48 J Biomed Mater Res 479–481 (1999).

* cited by examiner

*Primary Examiner*—Peter Nerbun
*Assistant Examiner*—Katherine Moran
(74) *Attorney, Agent, or Firm*—Knobbe Martens Olson & Bear LLP

(57) ABSTRACT

The present invention is related to methods and apparatus that can enhance the security of a suture knot by annealing a portion of the suture knot. Such a suture knot is less likely to fail by slippage. Advantageously, the methods and apparatus can operate in a liquid environment, such as the inside of a body. Conventional knots made from monofilament sutures exhibit an unfortunate tendency to slip or untie. A surgeon can tie a conventional monofilament suture using standard knot tying techniques and anneal the suture. The annealing can fuse the tails of the suture together, thereby preventing failure by slippage. In one embodiment, the annealing textures the surface of the monofilament tails, thereby increasing friction and resistance to slippage. In another embodiment, the annealing is applied to the last throw in the knot.

1 Claim, 10 Drawing Sheets

METHODS AND APPARATUS FOR ANNEALING SUTURES

RELATED APPLICATION

This application claims the benefit priority under 35 U.S.C. §119(e) of U.S. Provisional Application No. 60/143,532, filed Jul. 13, 1999, the entirety of which is hereby incorporated by reference.

BACKGROUND OF THE INVENTION

1. Field of the Invention

The present invention is generally related to surgery. In particular, the present invention relates to suturing with synthetic suture material.

2. Description of the Related Art

For many years, surgeons have reconnected tissue using suturing and other methods. Suturing is a surgical technique involving the connection of tissue by stitching the tissue together with a strand of appropriate suturing material. Synthetic or polymer sutures are among the class of appropriate suturing material.

Typically, a suture is prepared by piercing the suture through tissue on both sides of a wound, by pulling the ends of the suture to bring the sides of the wound together, and tying the suture into a knot. The knot preserves the tension on the suture to maintain the sides of the wound in approximation and allow the tissue to heal.

Generally, it is undesirable for the suture to slip and become untied. An improperly tied knot can slip and untie at a tension far lower than the tension required to break the suture. When the suture is internal to the body, replacement of the failed suture can require another surgery.

Synthetic sutures are available as monofilament (single strand) or polyfilament (multiple strands). Polyfilament sutures can exhibit less shape memory and more friction than monofilament sutures, thus rendering a conventional knot made from polyfilament suture relatively more resistant to slippage than a conventional knot made from monofilament suture.

However, monofilament sutures (sutures made from one strand) are preferred in many applications. One such application is arthroscopy, where a surgeon accesses the surgical area through a hollow tube known as a cannula. In arthroscopy, the surgeon passes a suture through the cannula to the tissue. Conventional arthroscopy tools do not permit the direct passage of a polyfilament suture, as the polyfilament suture is too flexible. Thus, to use a polyfilament suture, the surgeon must first pass a monofilament suture ("feeder line") first, and then pull the polyfilament suture through the tissue using the monofilament suture. Cumulatively, the extra steps of first passing monofilament sutures can undesirably add a significant amount of time to a surgical procedure and can increase the trauma and anesthesia risk endured by a patient. Surgeons also prefer monofilament sutures in situations where a wound site may be contaminated. In those situations, monofilament sutures can lessen the risk of infection.

One drawback to monofilament sutures is that knots tied with monofilament sutures can slip and become untied more readily than polyfilament suture. Monofilament suture has a smoother exterior surface than polyfilament suture and thus exhibits less friction to prevent a knot from slipping. Monofilament suture also tends to exhibit more "memory," i.e., monofilament suture has a greater tendency to return to a previous form, such as an untied form.

Prior techniques to improve the security of a knot made from a monofilament suture have proven inadequate. One prior technique includes tying a knot with extra throws to reduce the tendency of the knot to slip. Extra throws, however, disadvantageously increase the bulk of a suture, consume extra time to process, and require extra space, which is not always available.

Additionally, proper knot tying techniques are not always followed. For example, through inadvertence or inexperience, the disfavored and easily loosened "Granny knot" can be accidentally tied instead of a "Square knot," which is a relatively more secure knot.

SUMMARY OF THE INVENTION

Embodiments of the present invention advantageously improve the security of knots. Surgical knots tied in accordance with an embodiment of the present invention can be tied with fewer throws, in less time, with more security, and with more resistance to incorrectly tied throws. According to one embodiment, a monofilament knot in arthroscopy can advantageously combine the resistance to slippage of a polyfilament suture and yet retain the advantage of not requiring the extra step of passing a feeder line.

One embodiment of the present invention places the ends of a knot in contact with each other and fuses the ends together with heat. The extraneous end portions of the suture are then cut, leaving the fused portion behind to prevent the knot from slipping. Preferably, the fused portion is about 3 millimeters (mm) long. The heat can be advantageously applied in a liquid environment, such as inside a human body.

Another embodiment of the present invention applies heat to the limbs of the knot such that the limbs deform. The deformation renders the knot more resistant to slippage. Again, the heat can be applied within the liquid environment of a human body.

Another embodiment of the present invention applies heat to the last throw of the knot. The last throw of the knot already has strands in contact with each other. The applied heat fuses the strands together and inhibits the tendency for the knot to loosen through slippage. The heat can again be applied within a liquid environment.

BRIEF DESCRIPTION OF THE DRAWINGS

These and other features of the invention will now be described with reference to the drawings summarized below. These drawings and the associated description are provided to illustrate preferred embodiments of the invention, and not to limit the scope of the invention.

DETAILED DESCRIPTION OF THE PREFERRED EMBODIMENTS

Although this invention will be described in terms of certain preferred embodiments, other embodiments that are apparent to those of ordinary skill in the art, including embodiments which do not provide all of the benefits and features set forth herein, are also within the scope of this invention. Accordingly, the scope of the present invention is defined only by reference to the appended claims.

The following definitions and explanations provide background information pertaining to the technical field of the present invention. Additional definitions are provided throughout the detailed description.

Glossary of terms:
- limb: The ends of a suture are known as limbs. One limb is a post, and the other limb is a loop.
- post: The end (limb) of the suture that the knot is tied around.
- loop: The end (limb) of the suture that forms the knot by looping around the post.
- ears or tails: The ends of the suture after the knot is complete and the limbs are cut.
- throw: An at least 360-degree wrapping or weaving of two limbs. A throw is also known as a half-hitch. A knot is a combination of at least two throws.
- suture: In the art, the term "suture" may refer to either the tissue-sewing material or the "stitch" formed by that material.

A surgical suture or stitch is created by forming a tight loop around the tissue with suture material and tying a knot. The knot maintains the tension on the suture so that the suture loop can hold the tissue together. There are an almost endless variety of knot configurations. Generally, the variety of knots can be split into two categories: non-sliding knots and sliding knots.

Figure 1:
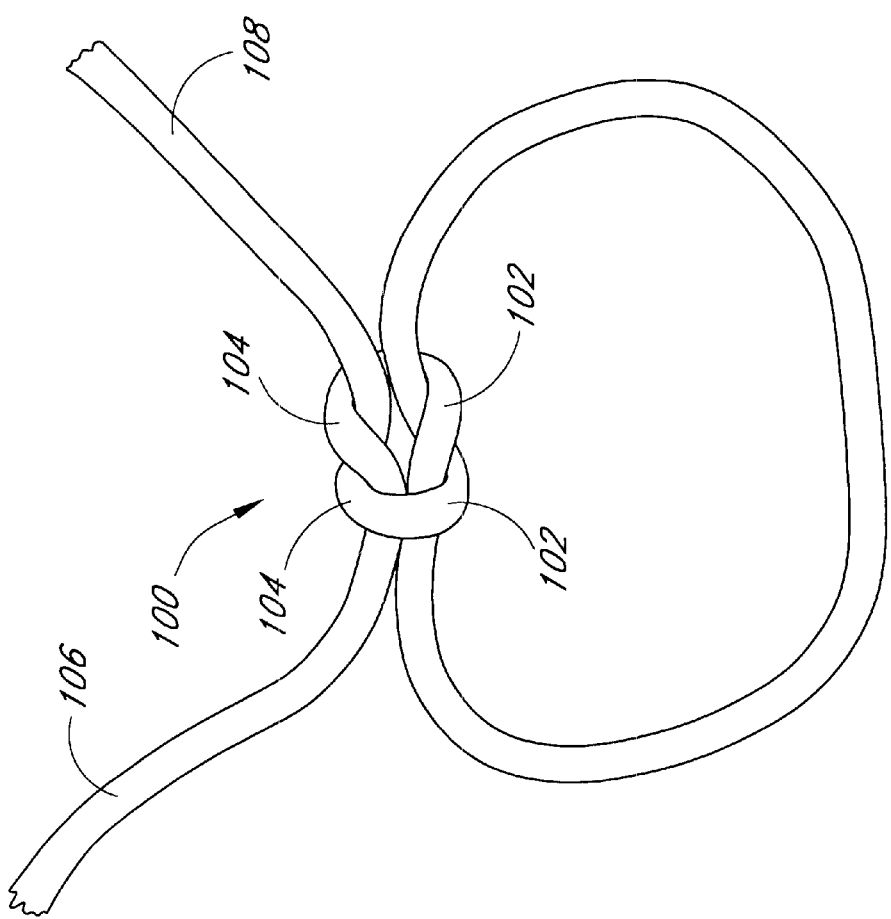
FIG. 1 illustrates a conventional Square knot.

FIG. 1 illustrates an example of a suture tied with a conventional non-sliding knot known as a Square knot 100. The Square knot 100 includes a first throw 102 and a second throw 104. Both the first throw 102 and the second throw 104 shown are made by looping the limbs of the suture 360 degrees. To make the knot "square," the second throw 104 is wrapped in the opposite rotational direction to the first throw 102. The Square knot 100 includes a first tail 106 and a second tail 108. If and when the Square knot 100 slips, the first and the second tails 106, 108 are drawn into the knot. Slippage itself is an undesirable trait and when severe enough, the knot fails by becoming untied. Well-known variations of the Square knot 100 include knots such as the friction or the surgeon's knot, where the first throw 102 makes a 720-degree wrap.

Figure 2:
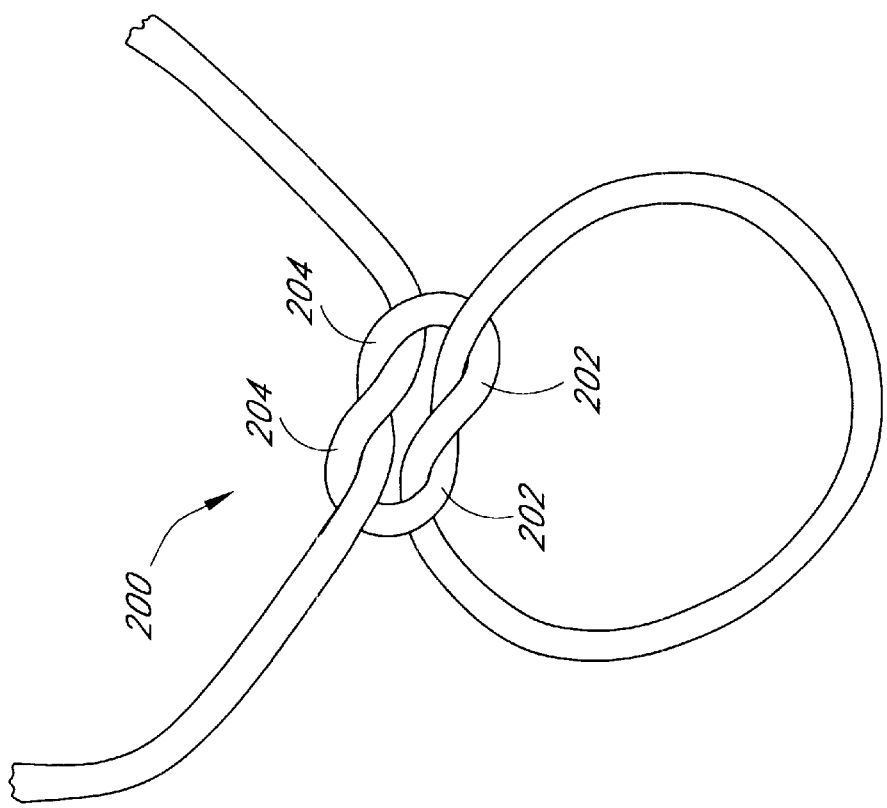
FIG. 2 illustrates a Granny knot.

FIG. 2 illustrates an example of a suture tied with a disfavored non-sliding knot known as a Granny knot 200. The Granny knot 200 is disfavored because it is notorious for slippage. The Granny knot 200 slips and becomes untied at a lower tension than the Square knot 100. The Granny knot 200 is constructed by rotating a first throw 202 and a second throw 204 in the same rotational direction. The Granny knot 200 is usually not an intended configuration, but rather, the result of an error.

Figure 4:
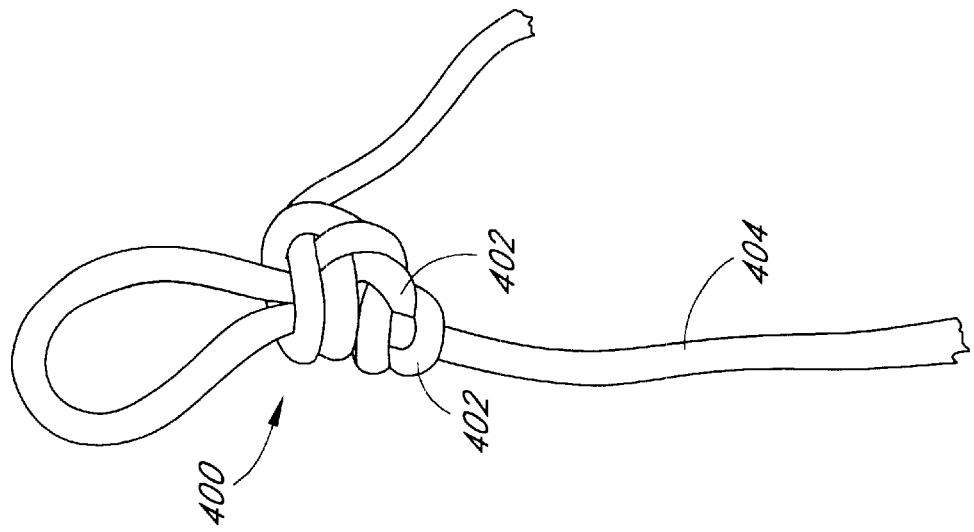
FIG. 4 illustrates 4 half-hitches with no alteration between throws.
Figure 3:
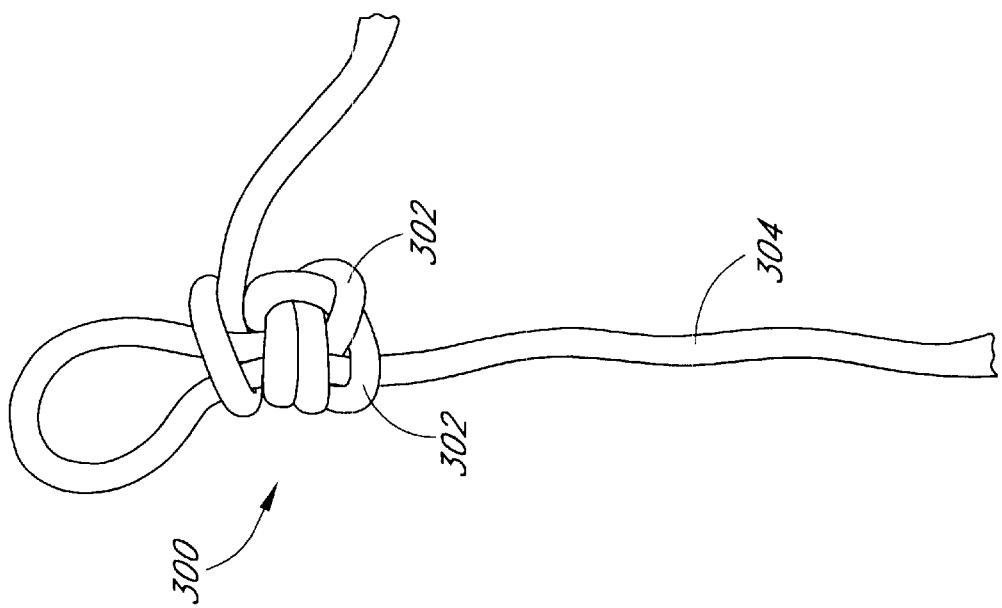
FIG. 3 illustrates 4 half-hitches with reversed throws.

FIGS. 3 and 4 are examples of conventional sliding knots. A sliding type of knot can be used when access to the environment is limited, such as in arthroscopy. A surgeon can pass the suture through a cannula and into tissue, then tie a sliding knot with the suture external to the body, then slide the knot down to the tissue, and then trim off the excess suture. FIG. 3 illustrates a four half-hitch knot 300, where the throws (the half-hitches) alternate directions between throws. FIG. 4 illustrates a four half-hitch knot 400, where the throws share a common direction. The four half-hitch knots 300, 400 are formed by throwing a half-hitch loop 302, 402 around a post 304, 404 four times to form the knot. After the knot is completed, the knot is pushed or pulled down the post 304, 404 to the tissue.

Figure 6:
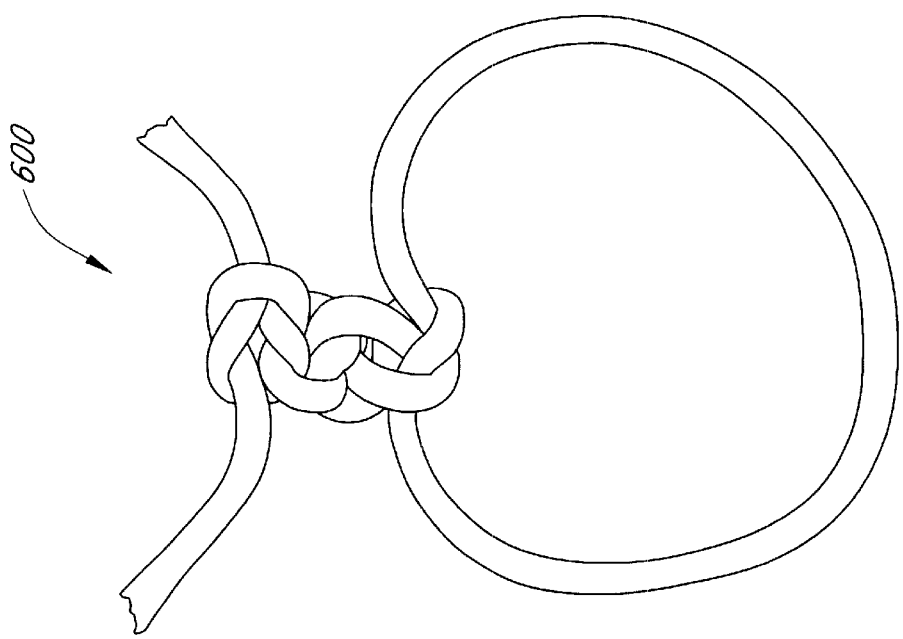
FIG. 6 illustrates a 5-throw Square knot.
Figure 5:
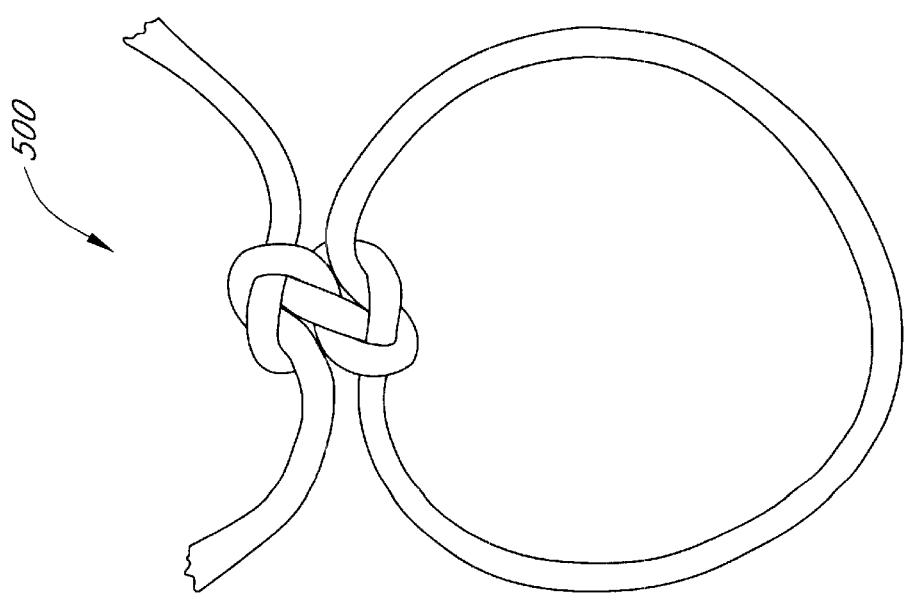
FIG. 5 illustrates a 3-throw Square knot.

One conventional technique used to improve the resistance to slippage of a knot is to use extra throws. FIGS. 5 and 6 illustrate knots with extra throws. FIG. 5 illustrates a Square knot formed with 3 throws 500. FIG. 6 illustrates a Square knot formed with 5 throws 600. Although additional throws can increase the resistance of a knot to slippage, the additional throws disadvantageously increase the bulk of the suture and require extra time. Furthermore, the extra space required to accommodate the extra throws is not always available.

A method according to one embodiment of the present invention can simply, quickly, and efficiently reduce the tendency for knots to slip without increasing the bulk of the suture. After a knot has been tied, portions of the ends of the knot are brought into contact with each other and fused together with heat.

The Square knot 100, described in connection with FIG. 1, will be used to illustrate the principles of the method described. It will be understood by one of ordinary skill in the art that the method can apply to all types of knots. A non-exhaustive list of types of knots includes: Square knots, Granny knots, Revo Knots, Half-Hitch knots, Duncan knots, Roeder knots, Lieurance Modified Roeder knots, and Tennessee Slider knots.

Figure 7:
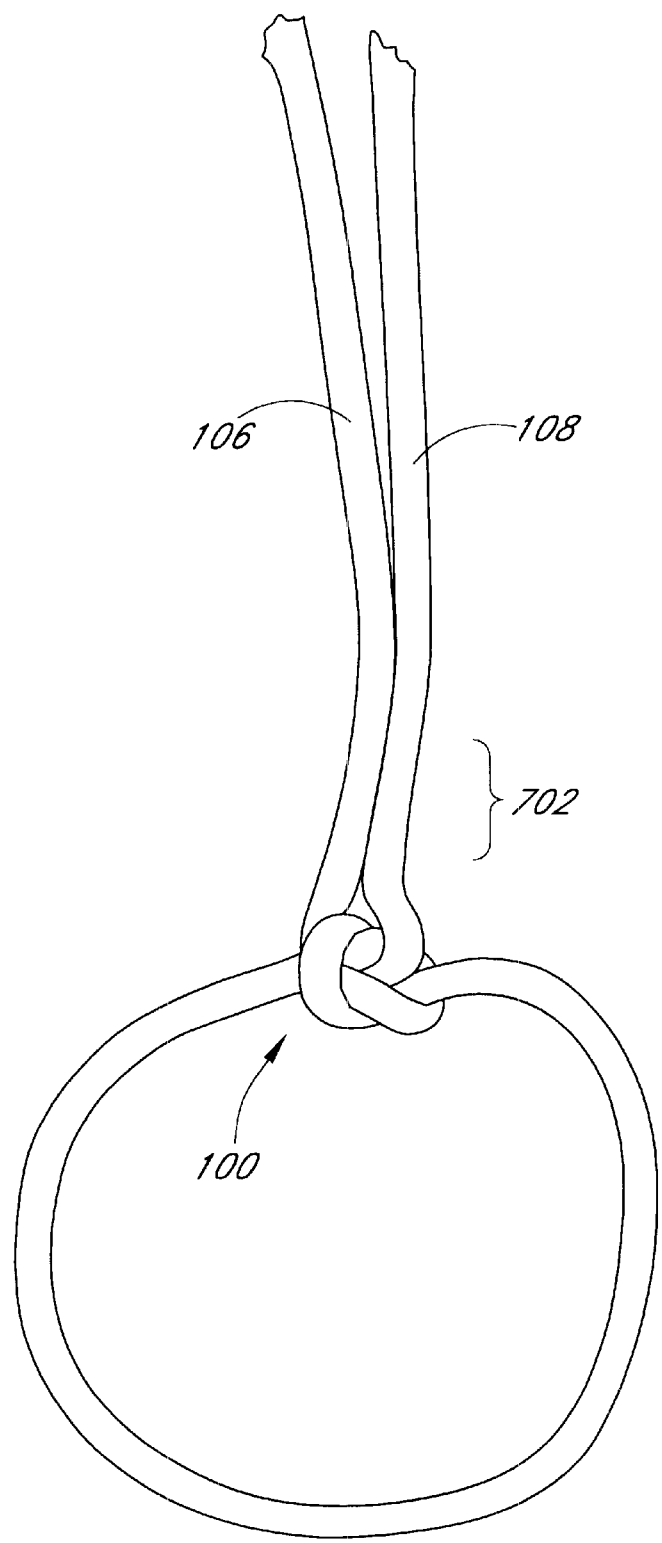
FIG. 7 illustrates the conventional Square knot with tails placed in contact.
Figure 8:
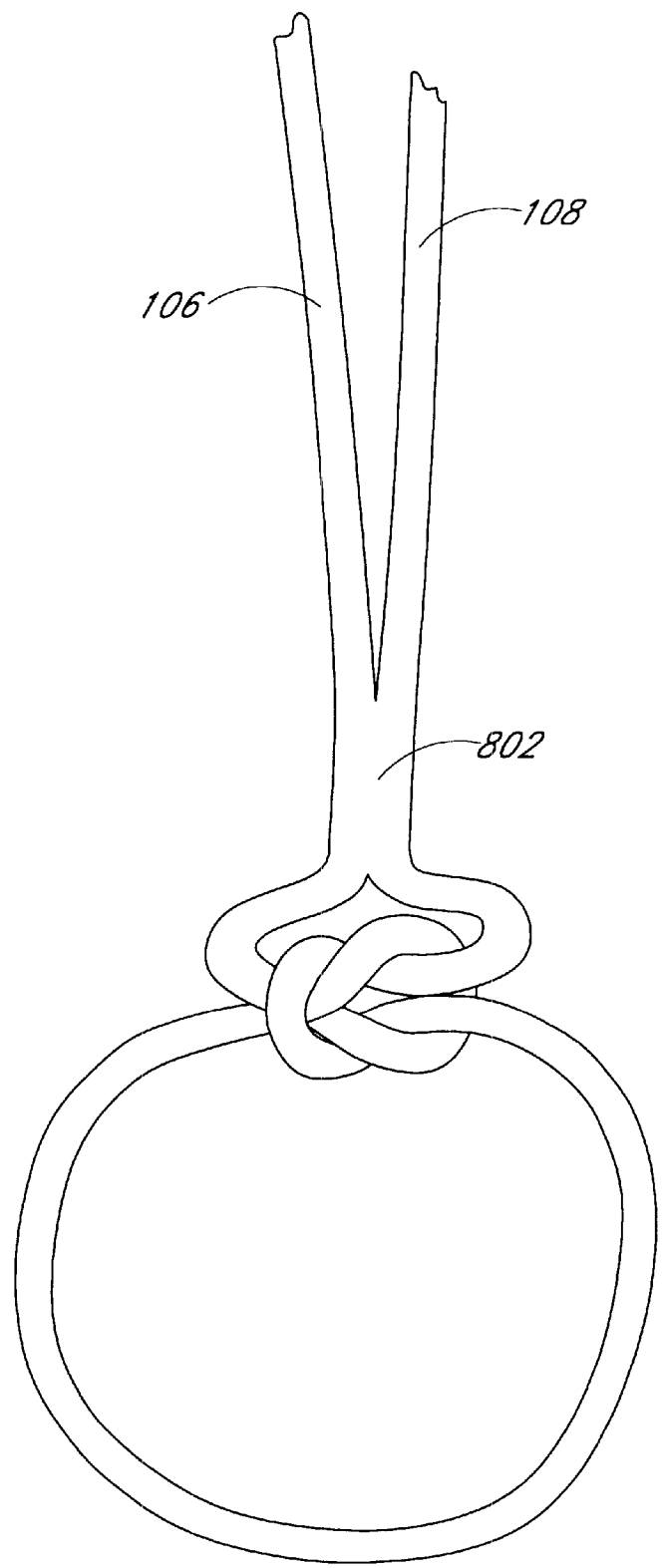
FIG. 8 illustrates the conventional Square knot with tails fused.
Figure 9:
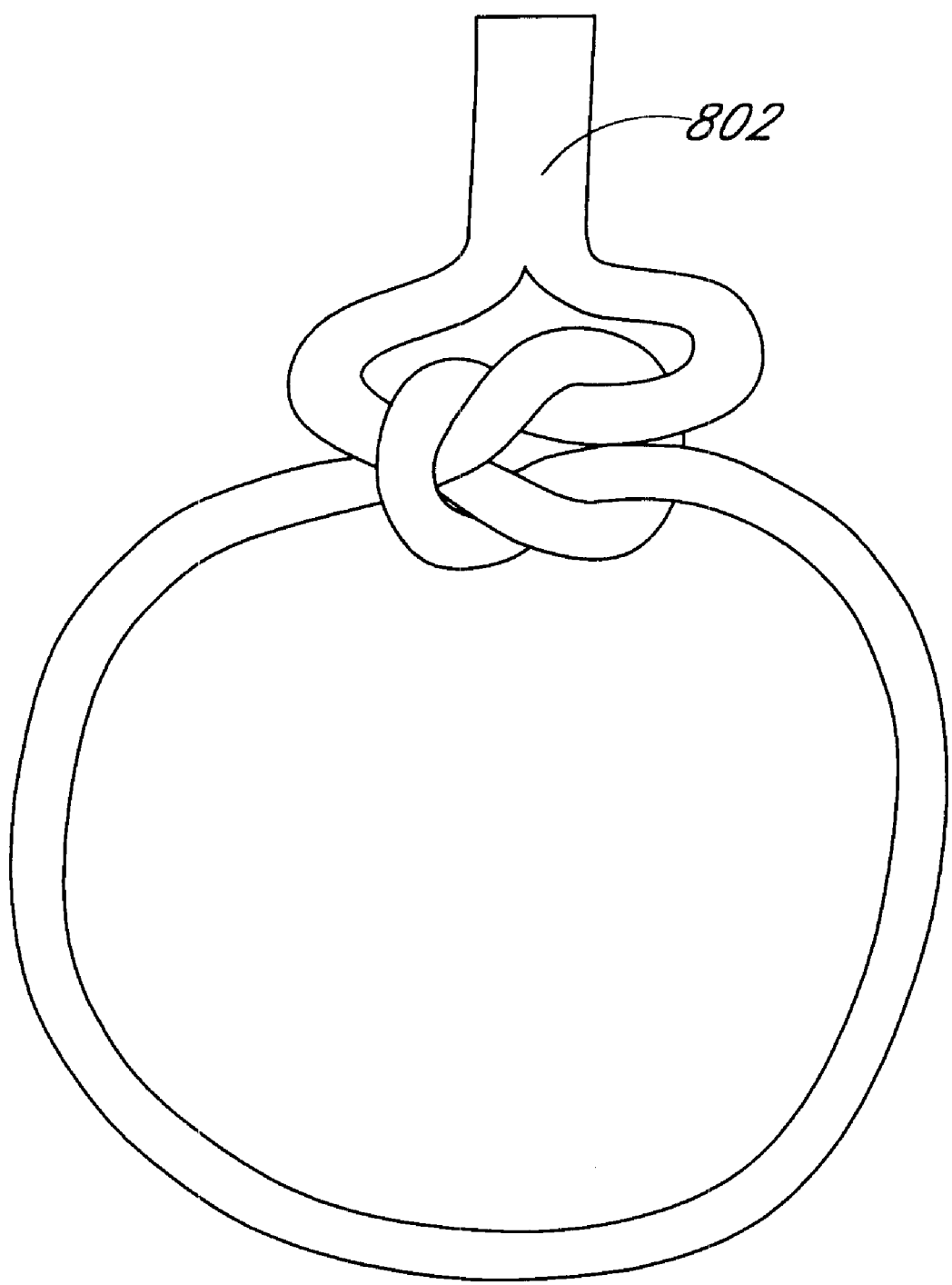
FIG. 9 illustrates the conventional Square knot with tails trimmed.

FIG. 7 illustrates the Square knot 100 with the first and the second tails 106, 108 brought into contact with each other in a first region 702. Preferably, the first region 702 is close to the knot 100. Following an application of heat to the first region 702, the first and second tails 106, 108 fuse together in the first region 702 and form a fused portion 802, as shown in FIG. 8. After the fusing operation is complete, the surgeon trims off the excess suture material in the remainder of the first and the second tails 106, 108 distal to the fused portion 802, as shown in FIG. 9. Of course, part of the trimmed material can include part of the fused portion 802. In one embodiment, a length of the fused portion 802 is approximately 3 millimeters (mm).

In one embodiment, the method is performed on the suture while the suture is submerged in a liquid environment, such as underwater. Such liquid environments exist, for example, within a human body. An added concern for the performance of the method in liquid is the relative increase in heat capacity and heat conductivity of a liquid, such as water, as compared to the heat capacity and heat conductivity of air. If adequate care is not taken to protect the surrounding tissue from the heat, tissue damage may result.

Of course, the temperature used to fuse the suture can vary with material, thickness, duration of application of heat, etc. In one embodiment, the temperature of an annealing (heating) device is set to about 99 degrees Centigrade (C) during the fusing procedure for a 0 PDS-II Polydiosanone suture material from Ethicon, Inc.

Applicants have verified the efficacy of the method by experiment. Four different knot configurations were tested, two of which were prepared in a conventional manner and the other two prepared in accordance with an embodiment of the invention. Each group consisted of twenty identically prepared sutures, each of which was tied from the same fresh batch of the 0 PDS-II Polydiosanone suture material (a synthetic monofilament) referenced above. For added consistency, each suture was tied around a caliper and presented a circumference of approximately 128.81 mm prior to test.

In the two groups where the tails of the sutures were annealed and fused, the sutures were placed in one-liter of Lactate Ringer solution at room temperature. The tails of the sutures were clamped and then annealed and fused. An Orotec ORA-50 Electrothermal Generator and a TAC-C Electrothermal probe, set at a temperature of 99 degrees C. and a power setting of 40, provided the heat for the annealing and fusion operation. The TAC-C Electrothermal probe was applied to the clamped tails while the clamped tails were immersed in the solution to anneal and fuse the tails.

The sutures were tested to failure with an Instron Model 8521 materials testing machine configured to measure ultimate tensile strength. The failure load data provided in Table 1, below, is in Newtons (N). Table 1 summarizes test results of the groups of knots.

TABLE 1

| Group | Knot Type | Annealing and fusion? | Failure Load (N) | Standard Error (N) | Failure Mechanism |
|---|---|---|---|---|---|
| 1 | 4 half-hitches | yes | 77.505 | 1.775 | breakage |
| 2 | 5 Square knots | no | 88.965 | 1.687 | breakage |
| 3 | 3-throw Square knots | no | 34.115 | 2.976 | slippage |
| 4 | 3-throw Square knots | yes | 78.210 | 1.723 | breakage |

Clearly, the suture knots in Groups 1, 2, and 4 exhibit relatively more strength than the suture knots in Group 3. Group 2 suture knots, which conform to the 5-throw suture knot described in connection with FIG. 6, are examples of conventional suture knots that use extra throws for enhanced security. Suture knots from Group 2 break, rather than slip.

Suture knots from Group 1, which conform to the four half-hitch knot 300 described in connection with FIG. 3 with the addition of the annealing and fusing of tails, also resisted slippage. The half-hitch knots used in Group 1 are typically resistant to slippage even without the annealing and fusion of the tails. The test results for Group 1 indicate that a secure conventional suture knot, such as that formed with a 4 half-hitch knot, is not weakened by the annealing and fusion of the tails.

The suture knots in Groups 3 and 4 conform to the 3-throw Square knot 500 described in connection with FIG. 5. The tails for the suture knots from Group 4 were additionally annealed and fused in accordance with an embodiment of the invention. The conventional 3-throw Square knot used in Group 3 failed due to slippage at a relatively insecure average of 34.115 Newtons (N). By contrast, the 3-throw Square knots, with annealing and fusion of the tails used in Group 4, did not fail until the sutures broke at a relatively secure average of 78.210 N. Significantly, the Group 4 knots would slip until held by the annealed and fused tails, at which point the knots tightened up until the sutures broke.

In another embodiment of the present invention, the tails of a knot, such as the first and the second tails 106, 108 of the Square knot 100, are annealed without fusing. The heat applied from the annealing textures the surface of the suture tails. As a result, the friction coefficient of a monofilament suture can increase and the security of a knot is enhanced.

Another embodiment advantageously anneals and fuses the top-most throw (the last throw made) of a knot. The strands of a suture knot are already in contact with each other in the knot, thus avoiding the need to bring two strands into contact with each other to fuse the strands into one strand.

Figure 10:
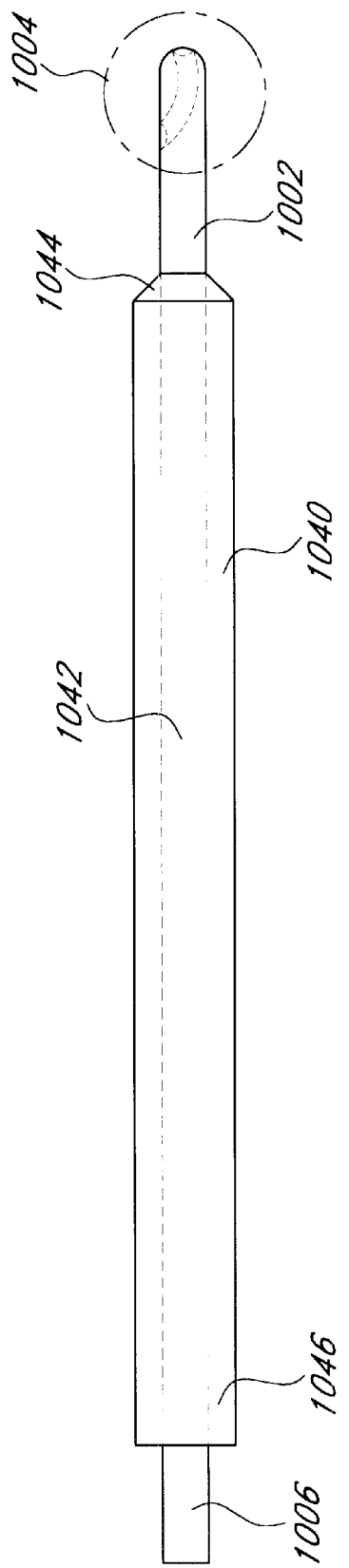
FIG. 10 illustrates an embodiment of the invention that can anneal the tails of a suture knot.

FIG. 10 illustrates one embodiment of the invention. An annealing element 1002 performs annealing and fusing to the tails of the suture and a cutter 1040 trims the excess lengths of the tails after annealing and fusion. The annealing element 1002 and the cutter 1040 shown in FIG. 10 are long and thin instruments suitable for passage through a hollow tube such as a cannula used in arthroscopy. The cutter 1040 contains a hollow cavity 1042 such that the annealing element 1002 can pass through the cutter 1040.

Figure 11A:
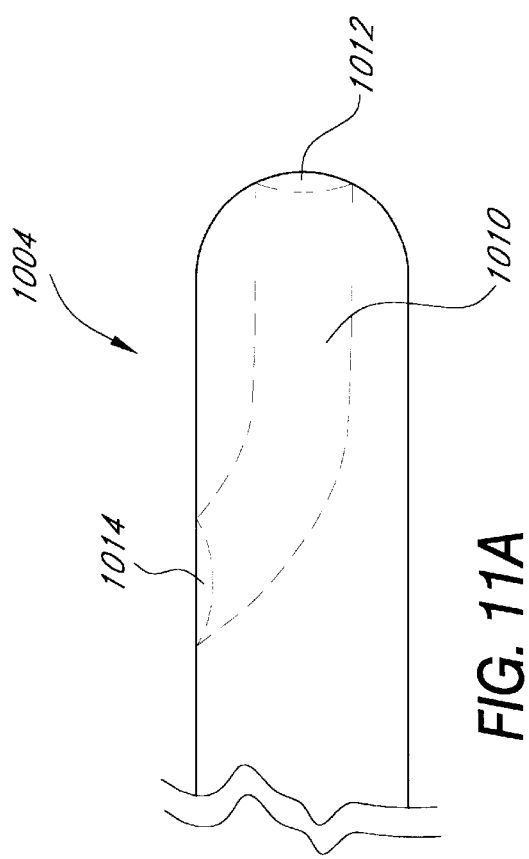
FIG. 11A illustrates a tip of an annealing element.

The annealing element 1002 includes a tip 1004 located at a distal end of the annealing element 1002. The tip 1004 of the annealing element 1002 heats and fuses the tails of the suture without excessive heating of the liquid environment. FIG. 11A illustrates the tip 1004 of the annealing element 1002 in greater detail. The tip 1004 includes a channel 1010 with a distal opening 1012 and a proximal opening 1014. The channel 1010 is a hollow tubular structure with a cross sectional area adapted to receive both tails of the suture. A cross section of the channel 1010 can be circular, elliptical, rectangular, or a variety of other shapes. In one embodiment, a path length of the channel 1010, as measured from the distal opening 1012 to the proximal opening 1014 is 3 mm.

Figure 11B:
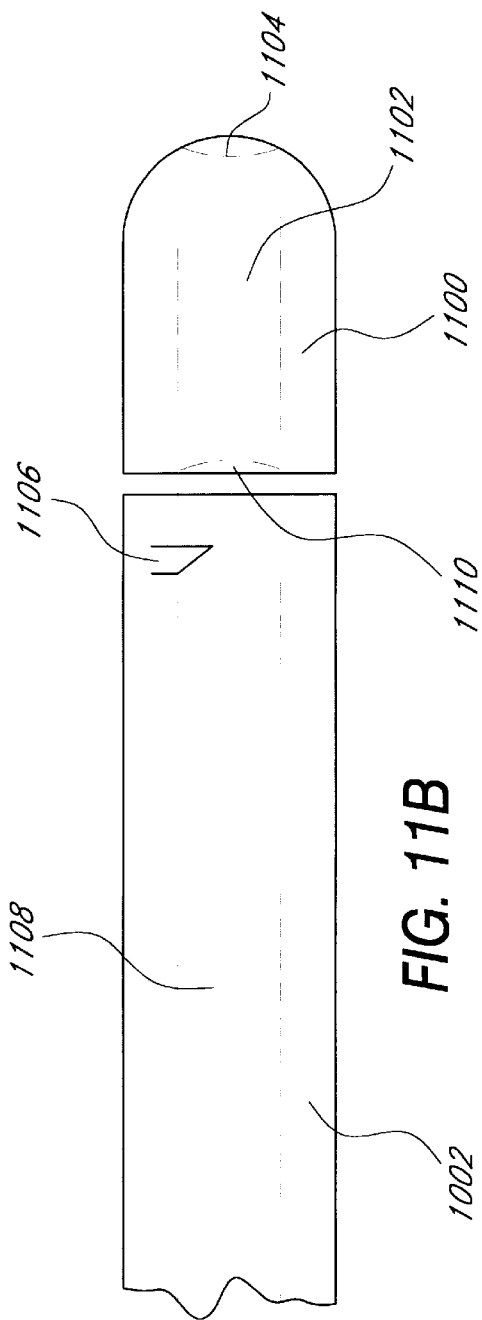
FIG. 11B illustrates another tip of the annealing element.

FIG. 11B illustrates an alternative embodiment of an annealing tip 1100. The annealing tip 1100 couples to the annealing element 1002 and the annealing tip 1100 includes a channel 1102 with a first opening 1104. The suture tails are fed through the first opening 1104, through the channel 1102 of the annealing tip 1100, out through a second opening 1110, and through a chamber 1108 in the annealing element 1002. The channels 1010, 1102 can take the form of tunnels, grooves or cutouts.

When the surgeon has positioned the first opening 1104 near to the suture knot, the surgeon can activate a heat source to anneal the portion of the suture tails in the channel 1102. A cutting tip 1106, preferably about 3 mm from the first opening 1104, cuts the excess length of the suture tails. The cutting tip 1106 can be located in the channel 1102, the chamber 1108, or in-between. In one embodiment, the surgeon rotates the cutter 1106 such that a sharp edge of the cutter slices the excess length of the suture tails. It will be understood that the cutter 1106 includes other forms of cutters that are well known in the art.

The channel 1010 is preferably formed within a material with a relatively high amount of thermal conductivity. In one embodiment, the channel 1010 is formed from stainless steel. The channel 1010 is thermally coupled to a heat source. One example of a heat source is a coil of Nichrome resistance wire, which heats in response to an application of electrical current. The coil of Nichrome wire can be wrapped around the channel 1010 to provide uniform heating. Conventional wires can electrically couple a power source for the Nichrome wire from a connector located at the proximal end 1006 of the annealing element 1006.

The power source can be a Direct Current (DC) source or an Alternating Current (AC) source and is preferably configurable to activate for a selectable momentary duration and a selectable power level. In one embodiment, the power level is controlled by adjusting a DC current limit of a current limit circuit within the power source. The current can be switched on and off by, for example, a MOSFET or bipolar transistor. The power source can be powered off of standard AC wiring or by batteries.

The tip may further include a heat sensor, such as a negative or positive temperature coefficient resistor, to provide the power source with a feedback of the annealing temperature. In one embodiment, the electrical components of the tip are electrically insulated from exterior surfaces of the annealing element 1002 such that a patient does not encounter a shock hazard. For example, a ceramic insulator such as alumina disposed between the channel 1010 and the heat source can provide electrical isolation and yet allow the heat source to transfer heat to the channel 1010. To further enhance electrical safety, the exterior surfaces of the annealing element 1010 (including the interior surface of the channel) can be tied to an electrical ground. One embodiment of the annealing element 1002 is substantially watertight so as to permit the submersion of at least a portion of the annealing element 1002 in liquid.

The remainder of the tip 1004 is preferably formed from a material that is relatively resistant to temperature and has a relatively low amount of thermal conductivity. A relatively low amount of thermal conductivity is preferred to limit the amount of heat transferred to the liquid environment. In one embodiment, the remainder of the tip 1004 is constructed from Teflon®, which is a trade name for polytetrafluoroethylene (PTFE). In another embodiment, only an exterior surface of the tip 1004 is insulated by the material resistant to temperature with a low thermal conductivity.

Typically, the tails of a knot in arthroscopy are quite long such that the surgeon can tie the knot outside the body and slide the knot down to the tissue. After the suture has been tied by the surgeon, the surgeon inserts the tails of the knot into the distal opening 1012 and out of the proximal opening 1014. The surgeon then slides the annealing element 1002 and the cutter 1040 down the cannula to the suture knot. The surgeon can manipulate the annealing element 1002 through the cutter 1040 or by grasping a proximal end 1006 of the annealing element 1002. Of course, a proximal end 1046 of the cutter 1040 or the proximal end 1006 of the annealing element 1002 can include grips and handles to facilitate handling.

Upon reaching the suture knot, the surgeon activates the heat source within the tip 1010, which anneals and fuses the tails. The surgeon then slides the cutter 1040 such that a sharp edge 1044, mounted at a distal end of the cutter 1040, cuts the excess length of the tails. The surgeon then withdraws the excess length of the tails, the annealing element 1002, and the cutter 1040.

In one embodiment, the application of heat from the channel 1010 to the suture tails is set low enough such that fusion of the suture tails does not occur. However, the heat provided is high enough to impart a surface texturing for the suture tails. The surface texturing of a monofilament suture can advantageously increase the friction coefficient of the suture tails such that the security of the knot is enhanced.

Figure 12:
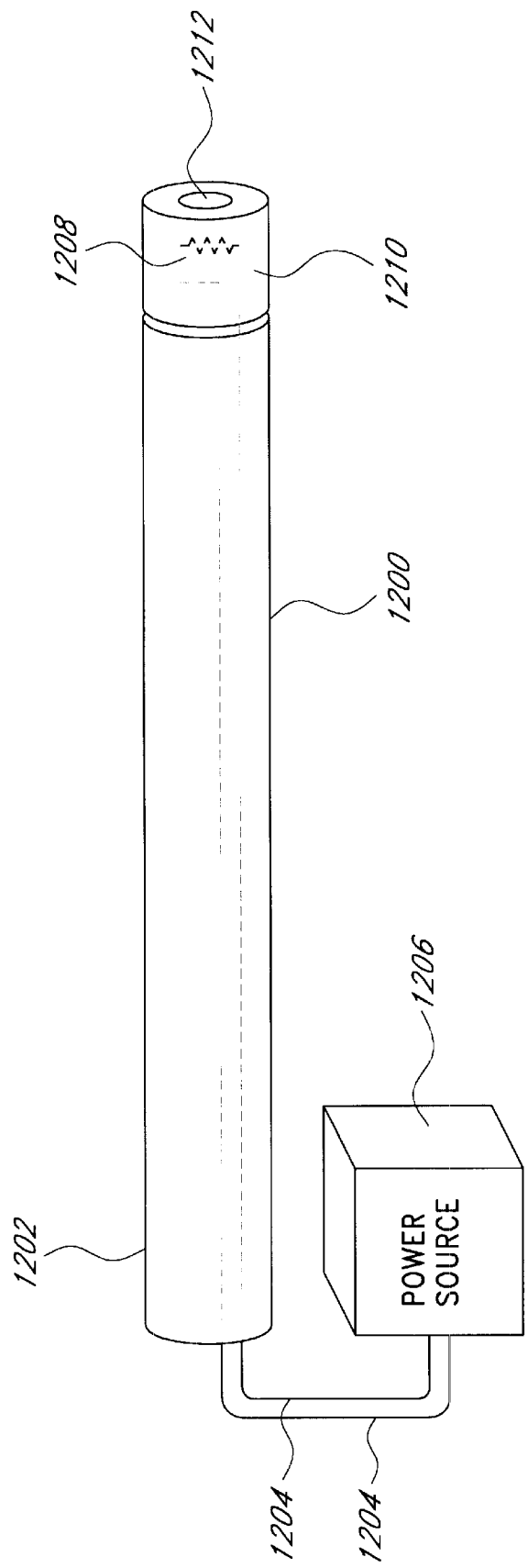
FIG. 12 illustrates an embodiment of the invention that can anneal the last throw of a suture knot.

FIG. 12 illustrates another embodiment of the invention. The annealer 1200 again includes a long thin structure to allow the annealer 1200 to pass through a cannula to tissue. A proximal end 1202 of the annealer 1200 connects through conventional wires 1204 to an electrical power source 1206. The wires pass through an interior cavity of the annealer 1200 to a heating element 1208. The heating element 1208 can be a Nichrome wire. The heating element 1208 is located in a tip 1210 of the annealer 1200. In one embodiment, the tip 1210 is integrated with the structure of the annealer 1200. The bulk of the tip 1210 can be insulated with Teflon® to limit inadvertent heating of the liquid environment.

A heating surface 1212 of the tip is thermally coupled to the heating element 1208 and applies heat to the top-most (last tied) throw of a suture knot. Preferably, the heating surface is constructed from a material with a relatively high amount of thermal conductivity, such as stainless steel. The heating surface 1212 can include a small portion of the area of the end of the tip, or the heating surface 1212 can include the entire area of the end of the tip. The heating surface 1212 can also feature a flat, concave, or convex shape to adapt to various shapes of knots.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of enhancing the security of a synthetic suture knot, the method comprising:

tying the suture to form the knot;

momentarily applying heat to a first area of a first limb of the knot in a liquid environment;

momentarily applying heat to a second area of a second limb of the knot in the liquid environment;

cutting the first limb such that a first short length of the first limb remains attached to the knot, where the first short limb includes at least a first portion of the first area;

cutting the second limb such that a second short length of the second limb remains attached to the knot, where the second short limb includes at least a second portion of the second area; and applying heat to a last throw of the knot such that a first portion of the last throw bonds to a second portion of the last throw.

* * * * *